United States Patent [19]

Traussnig et al.

[11] Patent Number: 4,968,611
[45] Date of Patent: Nov. 6, 1990

[54] EXTRACTING AGENTS FOR POLY-D(—)-3-HYDROXYBUTYRIC ACID

[75] Inventors: Heinz Traussnig, Frohnleiten; Engelbert Kloimstein, Eferding; Hans Kroath; Robert Estermann, both of Linz, all of

[73] Assignee: Petrochemie Danubia Gesellschaft m.b.H., Schwechat-Mannsworth, Austria

[21] Appl. No.: 370,367

[22] Filed: Jun. 22, 1989

[30] Foreign Application Priority Data

Jul. 7, 1988 [AT] Austria ................. 1759/88

[51] Int. Cl.$^5$ .................. C12P 7/62; C12P 7/42; G08G 63/06
[52] U.S. Cl. .................. 435/135; 435/146; 435/267; 528/361; 528/486; 528/492; 528/494; 528/495; 528/496
[58] Field of Search .............. 435/135, 146, 267; 528/486, 492, 494, 495, 496, 361

[56] References Cited

U.S. PATENT DOCUMENTS

| | | | |
|---|---|---|---|
| 3,036,959 | 5/1962 | Baptist | 435/146 |
| 3,044,942 | 7/1962 | Baptist | 435/146 |
| 3,275,610 | 9/1966 | Coty | 435/135 |
| 4,101,533 | 7/1978 | Lafferty et al. | 528/491 |
| 4,138,291 | 2/1979 | Lafferty et al. | 435/135 |
| 4,140,741 | 2/1979 | Lafferty et al. | 435/135 |
| 4,310,684 | 1/1982 | Vanlautem et al. | 528/361 |
| 4,336,334 | 6/1982 | Powell et al. | 435/146 |
| 4,358,583 | 11/1982 | Walker et al. | 435/135 |
| 4,562,245 | 12/1985 | Stageman | 435/135 |
| 4,705,604 | 11/1987 | Vanlautem et al. | 435/135 |
| 4,786,598 | 11/1988 | Lafferty et al. | |

FOREIGN PATENT DOCUMENTS

| | | |
|---|---|---|
| 15123 | 9/1980 | European Pat. Off. . |
| 0052459 | 5/1982 | European Pat. Off. . |
| 0069497 | 1/1983 | European Pat. Off. . |

OTHER PUBLICATIONS

Derwent Abstract, 88-273896/39, Mitsubishi Rayon KK, J63198991, 8-1988.
Derwent Abstract, 86-062260/10, Schmidt et al., DD-229428, (11-1985).
Derwent Abstract, 87-294832/42, Mitsubishi Rayon KK, J62205787, (9-1987).
Derwent Abstract, 87-029964/05, Schmidt et al., DD-239609, (10-1986).
Derwent Abstract, 89-055709/08, Mitsubishi Kasei, EP304293, (2-22-1989), Doi.
Japio Derwent Abst., 89-048820, Doi, J01048820, 2-2-3-89, Mitsubishi Kasei.
Japio Derwent Abst., 88-198991, Numazawa et al., J63198991.

Primary Examiner—Herbert J. Lilling
Attorney, Agent, or Firm—Mark Dryer

[57] ABSTRACT

Use of diols or acetalized triols, di- or tricarboxylic acid esters, mixtures of dicarboxylic acid esters or butyrolactone as extracting agents for obtaining pure polyesters or copolyesters containing 3-hydroxybutyric acid units.

7 Claims, No Drawings

EXTRACTING AGENTS FOR POLY-D(−)-3-HYDROXYBUTYRIC ACID

BACKGROUND TO THE INVENTION

The invention relates to the use of certain carboxylic acid esters and polyvalent alcohols as extracting agents for obtaining pure polyesters or copolyesters containing 3-hydroxybutyric acid units.

Poly-D(−)-3-hydroxybutyric acid (poly-HB) is synthesized and accumulated inside the cell by many microorganisms as a substance for storing energy and carbon and represents a polyester having thermoplastic properties which is biologically degradable. Poly-HB can, for example, be prepared in good yields without problems by the procedures described in U.S. Pat. No. 4,786.598.

Copolyesters of poly-HB, such as, for example, copolyesters consisting of 3-hydroxy-butyric acid and 3-hydroxyvaleric acid units and also other acid units should, according to EP-A-0,052,459, exhibit better processing properties than pure poly-HB when used as thermoplastics. A process for the preparation of such copolyesters is disclosed in EP-A-0,069,497.

The polyesters are present in the cell material of the microorganism after biological preparation and must then be extracted from the cell material. Until now, this caused considerable difficulties.

Thus, for example, in U.S. Pat. No. 3,036,959 or in U.S. Pat. No. 3,044,942, it is described that good yelds in the extraction of the polyester from the cell material of the microorganism can only be achieved if an additional step for disrupting the cells, in which the cells are treated with acetone, is introduced before the actual extraction step. Pyridine or methylene chloride must be used as extracting agents.

In U.S. Pat. No. 3,275,610, chloroform is described as an extracting agent. In order to achieve good yields, however, the cells must be treated for a very long time with the extracting agent. However, due to the long treatment, depolymerization of the poly-HB occurs so that either a poor yield or a reduction in the molecular weight of poly-HB must be taken into account in this method.

In U.S. Pat. No. 4,310,684, other halogenated hydrocarbons are proposed for the extraction. However, halogenated hydrocarbons are on the whole toxic and represent a hazard for any who have to work with them, and additionally a pollution of the environment, it also having to be taken into consideration that residual contents of this solvent in the isolated poly-HB are unavoidable.

In U.S. Pat. No. 4,101,533, cyclic carbonic acid esters such as ethylene carbonate or propylene carbonate were therefore proposed as solvents for polyhydroxybutyric acid. However, these solvents are very corrosive in the hot state in which they have to be used and attack taps and joints of apparatuses. A relatively long treatment of the cells with ethylene carbonate or propylene carbonate is necessary for a good yield in the extraction of poly-HB, a particularly large reduction in the molecular weight of the poly-HB or its copolyesters occurring, however, which has disadvantageous consequences for the use of poly-HB or its copolyesters as thermoplastics.

In contrast, solvents for the simple and problemfree extraction of poly-HB and its copolyesters could now be found, the use of which as extracting agents avoids the abovementioned disadvantages, the polyesters or copolyesters being obtained in an unexpected high purity of at least 98% in very good yields.

SUMMARY OF THE INVENTION

The invention accordingly relates to the use of diols or acetalized triols, di- or tricarboxylic acid esters, mixtures of dicarboxylic acid esters or butyrolactone as extracting agents for obtaining pure polyesters or copolyesters containing 3-hydroxybutyric acid units.

The diols according to the invention may be aliphatic straight-chain or branched diols having a chain length of 2 to 8 C atoms, it being possible for the aliphatic chain to be broken by one or two nitrogen atoms which may optionally be substituted by a methyl group. Preferred diols are, for example, propane-, butane- and hexanediols, ethylhexanediols, N-methyldiethanolamine, N,N-bis(2-hydroxyethyl)-1,3-diaminopropane, propanediols being particularly preferred. The acetalized triols according to the invention are preferably glycerol formal or 2,2-dimethyl-4-hydroxymethyl-1,3-dioxolane, glycerol formal being particularly preferred.

The acid components of the dicarboxylic acid esters according to the invention may consist of straight chain or branched, saturated or unsaturated, aliphatic or aromatic dicarboxylic acids having 2 to 8 C atoms, it being possible for the aliphatic chain to be substituted by one or more hydroxyl groups or by an acetyl group, or of azodicarboxylic acid. Possible alcohol components for the dicarboxylic acid ester are straight-chain or branched alkyl alcohols. Examples which may be mentioned are methyl, ethyl, propyl, butyl, pentyl and hexyl alcohols and their isomers. The tricarboxylic acid esters according to the invention are citric acid esters, suitable alcohol components being, for example, the abovementioned alcohols, or triacetin.

The di- or tricarboxylic acid esters may be symmetrical or unsymmetrical, preferably symmetrical esters. Preferred dicarboxylic acid esters are, for example, diethyl oxalate, dimethyl and diethyl malonates, dimethyl and diethyl succinates, dimethyl glutarate, dimethyl adipate, diethyl ethylmalonate, dimethyl maleate, dibutyl fumarate, diethyl phthalate, diethyl and dibutyl tartrates, dimethyl acetylsuccinate and diisopropyl azodicarboxylate, dimethyl and diethyl succinates being particularly preferred.

The extracting agents according to the invention may also be mixtures of the dicarboxylic acid esters described. A particularly preferred mixture is composed of dimethyl succinate, glutarates and adipates, preferably in the ratio 1:4:1. Butyrolactone is taken to mean gamma-butyrolactone.

DETAILED DESCRIPTION OF THE INVENTION

To obtain the pure polyester or copolyester, the cell material of the microorganism, which contains the polyesters or copolyesters containing the 3-hydroxbutyric acid units, is isolated from the fermenter or from the fermenter solution by customary methods, preferably by removing the fermenter solution by centrifugation. The separated cell material may be dried as usual, or the cell material is employed in the extraction step watermoist. Preferably, the cell material is employed watermoist, the water content of the cell material in general being 40 to 80% by weight. The cell material isolated from the fermenter is stirred in one of the extracting agents according to the invention and heated to temperatures of about 100° to 150° C. and stirred for 5 to 20 minutes at this temperature. The undissolved cell material is then separated from the hot extracting agent which contains the dissolved polyesters. The separation can be carried out by customary methods, the use of heated suction filters being advantageous, since the separation surprisingly takes place without problems and simply in this manner. The separated solution which contains the polyesters is then cooled, whereupon the polyesters gel, or the polyesters are precipitated crystalline by addition of precipitating agents such as, for example, water, methanol, ethanol, acetone or mixtures thereof. The isolation of the polyesters is carried out, for example, by filtering off, filtering off with suction, removing by centrifugation or squeezing off the liquid from gels. The isolated precipitate is then washed with water, methanol, ethanol, acetone or mixtures thereof, whereupon precipitated gels crystallize, and dried. The drying of the polyesters takes place in a customary manner, for example in a drying oven.

In a preferred embodiment, the cell material of the microorganism from the fermenter solution is removed by centrifugation, heated to 110° to 140° C. in propanediol, glycerol formal, dimethyl succinate or diethyl succinate, an ester mixture consisting of dimethyl succinate, glutarate and adipate or in butyrolactone and stirred for 15 minutes at this temperature. The undissolved cell material is separated by means of a heated suction filter and the hot solution is cooled, whereupon the polyester gels. However, a precipitating agent such as water, ethanol, methanol, acetone or mixtures thereof may also be added to the solution, whereupon the polyesters precipitate in crystalline form. The gels are isolated by filtering off with suction, it optionally still being additionally possible to squeeze off the liquid, and are crystallized by stirring the residue with a precipitating agent such as water, ethanol, methanol, acetone or mixtures thereof; the crystalline precipitate is filtered off with suction and dried. Since the extracting agents without exception have high boiling points compared to the precipitating agents, they can be recovered from the precipitating agents by, for example, distillation and both the precipitating and extracting agents can be employed afresh again and again in the extraction.

The use of the extracting agents according to the invention yields polyesters in an unexpectedly high purity of at least 98% in very good yields, only a remarkably low depolymerization of the polyester occurring, and the extraction being simple and problem-free to carry out and thus representing an enrichment of the art.

The following Examples illustrate the invention.

EXAMPLE 1

100 g of a water-moist cell material from the fermenter, obtained by removing the fermenter solution by centrifugation and having a water content of 60% by weight and a poly-HB content of 78% relative to the cell dry weight, were stirred for 10 minutes at 140° C. with 360 g of 1,2-propanediol. After separating the undissolved cell material by means of a heated suction filter, the solution was cooled, whereupon poly-HB gelled. The precipitated gel was filtered off with suction, stirred well with water and then washed, whereupon the gel crystallized, and the crystalline precipitate was filtered off with suction and dried. In this way, 24.6 g of poly-HB, which corresponds to 79% of theory, having a purity of 99.1% and a molecular weight of 585,000 were obtained, the molecular weight of the poly-HB in the cell material being 650,000.

EXAMPLE 2

25 g of a water-moist cell material from a fermenter, obtained by removing the fermenter solution by centrifugation, and having a water content of 60% by weight and a poly-HB content of 65% relative to the cell dry weight, were stirred at 120° C. for 15 minutes with 390 g of glycerol formal. After separating the undissolved cell material by means of a heated suction filter, the solution was cooled, whereupon poly-HB gelled. The precipitated gel was filtered off with suction and then washed with water and acetone, whereupon the gel crystallized, and the crystalline precipitate was filtered off with suction and dried. In this way, 5.5 g of poly-HB, which corresponds to 85% of theory, having a purity of 99.7% and a molecular weight of 700,000 were obtained, the molecular weight of the poly-HB in the cell material being 780,000.

EXAMPLE 3

25 g of a water-moist cell material from the fermenter, obtained by removing the fermenter solution by centrifugation, and having a water content of 60% by weight and a poly-HB content of 62% relative to the cell dry weight, were stirred for 15 minutes at 110° C. with 390 g of diethyl succinate. After separating the undissolved cell material by means of a heated suction filter, the solution was cooled, whereupon poly-HB gelled. The precipitated gel was filtered off with suction, then washed with water and ethanol, whereupon the gel crystallized, and the crystalline precipitate was filtered off with suction and dried. In this way, 5.6 g of poly-HB, which corresponds to 90% of theory, having a purity of 100% and a molecular weight of 400,000 were obtained, the molecular weight of the poly-HB in the cell material being 470,000.

EXAMPLE 4

25 g of a water-moist cell material from the fermenter, obtained by removing the fermenter solution by centrifugation, and having a water content of 60% by weight and a poly-HB content of 62% relative to the cell dry weight, were stirred for 15 minutes at 110° C. with 390 g of dimethyl succinate. After separating the undissolved cell material by means of a heated suction filter, the solution was cooled and methanol was added, whereupon poly-HB was precipitated. The deposited precipitate was filtered off with suction, then washed with water and acetone and dried. In this way, 5.3 g of poly-HB, which corresponds to 86% of theory, having a purity of 99.9% and a molecular weight of 420,000 were obtained, the molecular weight of the poly-HB in the cell material being 470,000.

EXAMPLE 5

25 g of a water-moist cell material from the fermenter, obtained by removing the fermenter solution by centrifugation, and having a water content of 60% by weight and a poly-HB content of 62% relative to the cell dry weight, were stirred for 15 minutes at 120° C. with 390 g of a mixture consisting of dimethyl succinate:dimethyl glutarate:dimethyl adipate in the ratio 1:4:1. After separating the undissolved cell material by means of a heated suction filter, the solution was cooled and ethanol was added, whereupon poly-HB precipitated. The precipitate was filtered off with suction, then washed with ethanol and dried. In this way, 5.5 g of poly-HB, which corresponds to 89% of theory, having a purity of 98.9% and a molecular weight of 725,000 were obtained, the molecular weight of the poly-HB in the cell material being 780,000.

EXAMPLE 6

125 g of a water-moist cell material from the fermenter, obtained by removing the fermenter solution by centrifugation, and having a water content of 60% by weight and a poly-HB content of 62% relative to the cell dry weight, were stirred at 110° C. for 15 minutes with 450 g of butyrolactone. After separating the undissolved cell material by means of a heated suction filter, the solution was cooled, whereupon the poly-HB gelled. The precipitated gel was filtered off with suction and then washed with water and acetone, whereupon the gel crystallized, and the crystalline precipitate was filtered off with suction and dried. In this way, 28 g of poly-HB, which corresponds to 90% of theory, having a purity of 99.5% and a molecular weight of 735,000 were obtained, the molecular weight of the poly-HB in the cell material being 780,000.

EXAMPLE 7

50 g of a water-moist cell material from the fermenter, obtained by removing the fermenter solution by centrifugation, and having a water content of 60% by weight and a content of a copolyester of 77.3% relative to the cell dry weight, the copolyester being composed of 98.1% of D(−)-3-hydroxybutyric acid and 1.9% of 3-hydroxyvaleric acid units, were stirred at 110° C. for 15 minutes with 400 g of dimethyl succinate. After separating the undissolved cell material by means of a heated suction filter, the solution was cooled and the copolyester was precipitated by addition of methanol. The deposited precipitate was filtered off with suction and then washed with water and acetone. In this way, 12.3 g of copolyester, which corresponds to 80% of theory, which was composed of 98.1% of D(−)-3-hydroxybutyric acid and 1.9% of 3-hydroxyvaleric acid units, having a purity of 100% and a molecular weight of 770,000 were obtained, the molecular weight of the copolyester in the cell material being 800,000.

EXAMPLE 8

50 g of a water-moist cell material from the fermenter, obtained by removing the fermenter solution by centrifugation, having a water content of 60% by weight and a content of a copolyester of 77.3% relative to the cell dry weight, the copolyester being composed of 98.1% of D(−)-3-hydroxybutyric acid and 1.9% of 3-hydroxyvaleric acid units, were stirred at 110° C. for 15 minutes with 400 g of a mixture consisting of dimethyl succinate:dimethyl glutarate:dimethyl adipate in the ratio 1:4:1. After separating the undissolved cell material by means of a heated suction filter, the solution was cooled and the copolyester was precipitated by addition of methanol. The deposited precipitate was filtered off with suction, then washed with water and acetone and dried. In this way, 13.9 g of copolyester, which corresponds to 90% of theory, which was composed of 98.1% of D(−)-3-hydroxybutyric acid and 1.9% of 3-hydroxyvaleric acid units, having a purity of 100% and a molecular weight of 785,000 were obtained, the molecular weight of the copolyester in the cell material being 800,000.

In the Examples, the polyhydroxybutyric acid determination was carried out by the method of Braunegg et al., Eur. J. Appl. Microbiol. Biotechnol. 6, 29 to 37, (1978).

The molecular weight determination was carried out by means of gel chromatography (PL microgel M, 60 cm column, 1 g/l in chloroform, 1 ml/min, polystyrene standards, density detection). The water content was determined by loss on drying.

What we claim is:

1. In a process for the preparation of a polyester or copolyester containing 3-hydroxybutyric acid units by cultivation of a poly-D(−)-3-hydroxybutyric acid producing microorganism in a fermentation medium and subsequent extraction and recovery of the desired product, the improvement which comprises using as an extracting agent a solvent selected from the group consisting of diols and acetalized triols, di- or tricarboxylic acid esters, mixtures of dicarboxylic acid esters, and butyrolactone to obtain said polyester or copolyester in substantially pure form.

2. A process according to claim 1, in which said extracting agent is propanediol.

3. A process according to claim 1, in which said extracting agent is glycerol formal.

4. A process according to claim 1, in which said extracting agent is dimethyl succinate or diethyl succinate.

5. A process according to claim 1, in which said extracting agent is a mixture of dimethyl succinate, dimethyl glutarate and dimethyl adipate.

6. A process according to claim 1, in which said extracting agent is butyrolactone.

7. A process according to claim 1, in which cell material of said microorganism is removed from said fermentation medium, heated to a temperature of from about 110° to 140° C. in said extracting agent, the resulting solution cooled and, after removing undissolved cell material, the desired product is precipitated and recovered from said solution.

* * * * *